US00PP18980P2

(12) United States Plant Patent
Kawashima et al.

(10) Patent No.: US PP18,980 P2
(45) Date of Patent: Jun. 24, 2008

(54) ***OSTEOSPERMUM* PLANT NAMED 'KAKEGAWA AU20'**

(50) Latin Name: *Osteospermum hybrida*
Varietal Denomination: Kakegawa AU20

(75) Inventors: Moriya Kawashima, Matsumoto (JP); Akinobu Ui, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 11/703,579

(22) Filed: Feb. 7, 2007

(51) Int. Cl.
*A01H 5/00* (2006.01)

(52) U.S. Cl. ..... Plt./360
(58) Field of Classification Search ..... Plt./360
See application file for complete search history.

*Primary Examiner*—Annette H Para
(74) *Attorney, Agent, or Firm*—Jondle & Associates, P.C.

(57) ABSTRACT

An *Osteospermum* cultivar particularly distinguished by its creamy yellow color, vigorous growth, plant structure with minimal branching and earliness to flower.

1 Drawing Sheet

Genus and species: *Osteospermum hybrida.*
Variety denomination: 'Kakegawa AU20'.

BACKGROUND OF THE NEW PLANT

'Kakegawa AU20' originated from a hybridization of proprietary hybrid *Osteospermum* breeding line 'G-769' (unpatented) and proprietary hybrid *Osteospermum* line 'SL-4' (unpatented) in Kakegawa, Japan. The male parent, 'SL-4', has a lemon yellow flower color, a plant growth habit with less branching and maintains its ability to flower under high temperature conditions, but does not have tolerance to highly humid conditions. The female parent, 'G-769', has a deep yellow flower color and does not bloom adequately under high temperature conditions.

In 2000, the two *Osteospermum* lines were crossed and 28 ovules were removed from flowers on the female parent and cultured by standard ovule culture techniques. A total of 3 plantlets were developed. The 3 $F_1$ hybrid plantlets were transplanted to soilless media for greenhouse culture and acclimatization. In 2001, the plants were evaluated and found to be cream yellow in flower color and to demonstrate an earliness to flower. Out of the 3 $F_1$ lines, the breeder selected line 'K3-102' which has a creamy yellow flower color, vigorous performance, a plant structure with minimal branching, is early to flower and maintains its ability to flower under high temperature conditions.

In fall 2002, the line 'K3-102' was vegetatively propagated with cuttings and re-evaluated in an open field and a greenhouse. The selection subsequently was named 'Kakegawa AU20' and found to retain its distinctive characteristics through successive asexual propagations in Kakegawa, Japan and Salinas, Calif.

Plant Breeder's Rights for this cultivar were applied for in Canada on Mar. 31, 2006.

SUMMARY OF THE INVENTION

The following are the most outstanding and distinguishing characteristics of this new cultivar when grown under normal horticultural practices in Kakagawa, Japan.

1. Creamy yellow flower color;
2. Vigorous growth;

3. Plant structure with minimal branching; and
4. Earliness to flower.

DESCRIPTION OF PHOTOGRAPHS

This new *Osteospermum* plant is illustrated by the accompanying photographs which show the plant's form, foliage and flowers. The colors shown are as true as can be reasonably obtained by conventional photographic procedures.

DESCRIPTION OF THE NEW CULTIVAR

Figure 1:
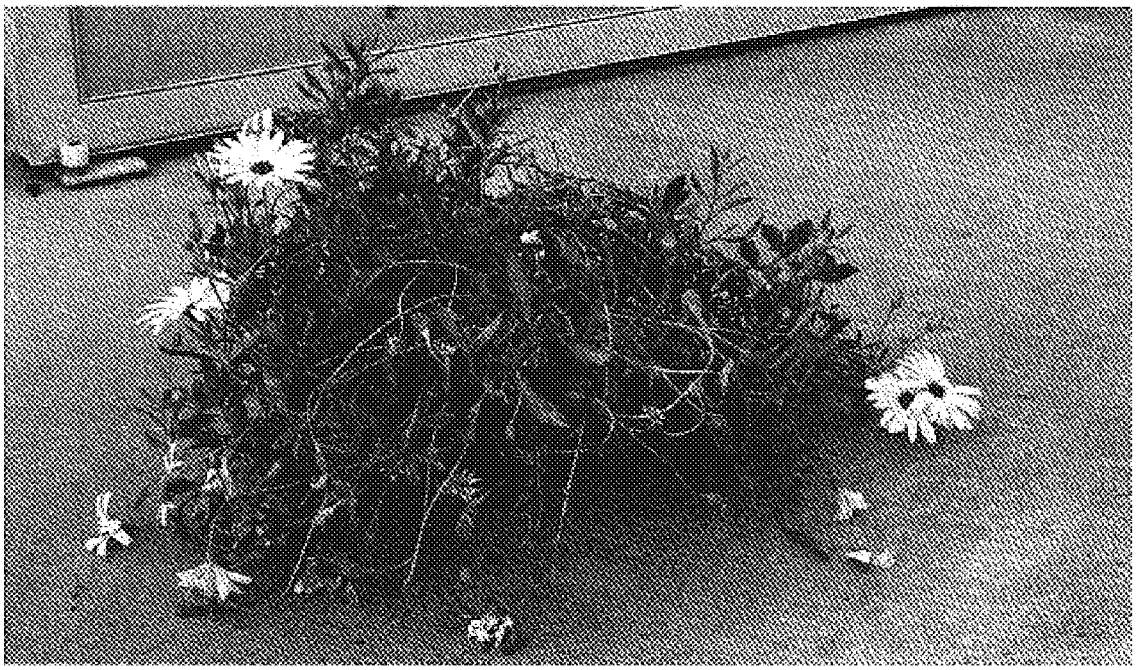
FIG. 1 shows overall plant habit.
Figure 2:
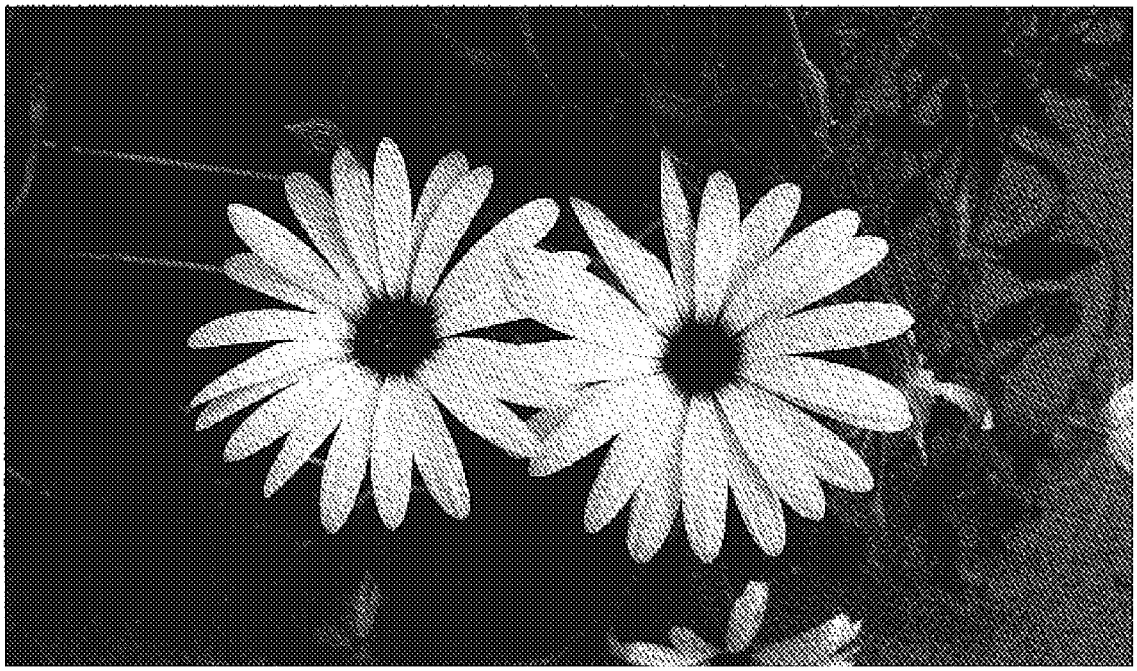
FIG. 2 shows the mature inflorescence.

The following detailed descriptions set forth the distinctive characteristics of 'Kakegawa AU20'. The data which define these characteristics were collected from asexual reproductions carried out in Salinas, Calif. Data was collected on plants grown approximately five months from transplanting rooted cuttings into 6-inch pots under greenhouse conditions in Salinas, Calif. Color references are to the R.H.S. Colour Chart of The Royal Horticultural Society of London (R.H.S.)

DESCRIPTION OF THE NEW PLANT

Classification:

*Family.*—Compositae.

*Botanical.*—*Osteospermum hybrida.*

Parentage:

*Female.*—Hybrid proprietary *Osteospermum* line 'G-769' (unpatented).

*Male.*—Hybrid proprietary *Osteospermum* line 'SL-4' (unpatented).

Growth:

*Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) of DIP 'N GROW root-inducing solution in water. The trays are misted hourly during rooting.

*Environmental conditions for plant growth.*—Rooted cuttings are transplanted to pots with a 16 cm diameter, one plant per pot. Peat-based growing media is used. The pots are watered using a 150–200 ppm fertilizer solution containing 18% nitrogen, 8% phosphorus and 18% potassium. The soil is allowed to dry between waterings. During the first few weeks after transplanting, the plants should have evening temperatures around 15–18° C. for good root growth. When plants reach 7.5–10 cm in height they are pinched back to 5–6 leaves to promote branching. Spring and summer daytime high temperatures in Salinas, Calif., where the data was collected, range from 16–25° C.

*Time to bloom from propagation.*—Approximately four weeks when rooted vegetative cuttings are transferred to a 16-cm. diameter pot. Flowering season is all year in the United States. Vernalization is not required to induce flowering.

Plant Description:

*Habit.*—Prostrate.
*Life cycle.*—Perennial.
*Form.*—Branching.
*Height.*—30 cm.
*Width.*—60 cm to 100 cm.

Stems:

*Internode length.*—2.0 cm.
*Stem description.*—Strong.
*Stem diameter.*—0.3 cm to 0.4 cm.
*Stem color.*—RHS 143C (Green).
*Pubescence.*—Sparse.
*Pubescence shape.*—Linear.
*Pubescence color.*—RHS N155A (White).

Leaves:

*Arrangement.*—Alternate.
*Shape.*—Oblanceolate.
*Apex.*—Acute.
*Base.*—Decurrent.
*Margin.*—Serrate.
*Venation.*—Pinnate.
*Surface.*—Dull, smooth.
*Surface pubescence.*—Present.
*Length.*—5.5 cm to 9.5 cm.
*Width.*—1.5 cm to 4.0 cm.
*Thickness.*—0.1 cm.
*Color.*—Upper surface: RHS 137A (Green). Lower surface: RHS 138B (Green).
*Venation color.*—Upper surface: RHS 139C (Green). Lower surface: RHS 138B (Green).

Inflorescence:

*Type.*—Capitulum (head); Disc florets are perfect and ray florets are carpellate.
*Flowering habit.*—Determinate.
*Lastingness of flowers.*—3 to 4 days.
*Fragrance.*—None.
*Seed production.*—None observed.
*Diameter.*—7.5 cm to 8.0 cm.
*Depth.*—1.5 cm to 2.0 cm.
*Disc diameter.*—0.7 cm to 1.0 cm.
*Disc floret number.*—55 to 65 per head.
*Peduncle length.*—20 cm to 30 cm.
*Peduncle diameter.*—0.2 cm.
*Peduncle color.*—RHS 138A (Green).
*Peduncle texture.*—Dull, slight pubescence.
*Phyllaries.*—Arrangement: 14 per inflorescence, free, arranged symmetrically. Length: 1.0 cm to 1.2 cm. Width: 0.15 cm. Apex: Acute. Margin: Entire. Shape: Linear, acute. Color: Upper surface: RHS 137B (Green). Lower surface: RHS 138B (Green).

Ray florets (Ligules):

*Corolla.*—One petal per ray floret; only the outer row of florets are the ray florets.
*Number of ray florets per inflorescence.*—15 to 20.
*Petal length.*—4.2 cm to 4.5 cm.
*Petal width.*—0.35 cm to 0.40 cm.
*Petal shape.*—Spatulate.
*Petal apex.*—Obtuse with a notched tip.
*Petal margin.*—Entire.
*Petal color.*—Upper surface: RHS 6D (Yellow) with RHS 155A (White) base that fades into RHS N79B (Purple) alongside the ray flowers and the very base of the petal. Lower surface: RHS 12C (Yellow) with RHS 167C (Grey-orange) streaks.
*Petal pubescence.*—Glabrous.
*Ovary: Superior.*
*Pistil form.*—One style with two stigma branches.
*Pistil length.*—0.3 cm.
*Stigma color.*—RHS N79B (Purple).
*Style color.*—RHS N80C (Purple-violet).

Disc florets:

*Color.*—RHS N88A (Violet).
*Shape.*—Tubular.
*Apex.*—Rounded.
*Surface.*—Smooth, shiny.
*Size.*—Length: 0.4 cm. Width: 0.1 cm.
*Pistil form.*—One style with two stigma branches.
*Ovary: Superior.*
*Style color.*—RHS N80C (Purple-violet).
*Stigma color.*—RHS N79B (Purple).
*Stamens.*—5, fused into a single tube.
*Anther color.*—RHS N79B (Purple).
*Pollen color.*—RHS 25B (Orange).

Disease and insect resistance: Very disease resistant, however, plants are susceptible to aphids, thrips, whiteflies and worms.

COMPARISON WITH PARENTAL LINES AND KNOWN CULTIVARS

'Kakegawa AU20' is a distinct variety of *Osteospermum* owing to its creamy yellow color, vigorous growth, plant structure with minimal branching and earliness to flower. 'Kakegawa AU20' is distinguished from its parents primarily by ray floret color and plant growth habit as described in Table 1 below (color references are to The Royal Horticultural Society Colour Chart, 4$^{th}$ edition):

| Characteristic | 'Kakegawa AU20' | Male Parent 'SL-4' | Female Parent 'G-769' |
|---|---|---|---|
| Ray floret (ligule) color, upper surface: | Creamy yellow | Lemon yellow | Deep yellow |
| Habit | Less branching | Less branching | Basal branching |

'Kakegawa AU20' is most similar to the *Osteospermum* plant named 'Seikilrem' (U.S. Plant Pat. No. 13,407); however, there are differences as described in Table 2 below (color references are to The Royal Horticultural Society Colour Chart, 4$^{th}$ edition):

TABLE 2

| Characteristic | 'Kakegawa AU20' | 'Seikilrem' |
|---|---|---|
| Ray floret (ligule) color, upper surface: | RHS 6d (Yellow) with RHS 155A (White) base that fades into RHS N79B (Purple) alongside the ray flowers and the very base of the petal. | RHS 12A (Yellow) at apex; RHS 12B mid section; RHS 155C towards base (White), band; below white band, RHS 90D to RHS 90B, (band of Purple) main color does not fade with subsequent development |

TABLE 2-continued

| Characteristic | 'Kakegawa AU20' | 'Seikilrem' |
|---|---|---|
| Habit | Less branching habit, vigorous growth performance | Compact and mounded plant habit; initially upright and then outwardly spreading. Moderately vigorous. |

I claim:

1. A new and distinct cultivar of *Osteospermum* plant as shown and described herein.

* * * * *